(12) United States Patent
Feniou et al.

(10) Patent No.: US 11,028,037 B2
(45) Date of Patent: Jun. 8, 2021

(54) METHOD OF REMOVING NITRATE COMPOUNDS FROM ADIPIC ACID

(71) Applicant: BASF SE, Ludwigshafen am Rhein (DE)

(72) Inventors: Romain Feniou, Lyons (FR); Mathieu Oullion, Lyons (FR)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/956,252

(22) PCT Filed: Dec. 13, 2018

(86) PCT No.: PCT/EP2018/084764
§ 371 (c)(1),
(2) Date: Jun. 19, 2020

(87) PCT Pub. No.: WO2019/121325
PCT Pub. Date: Jun. 27, 2019

(65) Prior Publication Data
US 2020/0317595 A1    Oct. 8, 2020

(30) Foreign Application Priority Data

Dec. 22, 2017   (EP) .................................. 17306899

(51) Int. Cl.
*C07C 51/27* (2006.01)
*B01J 8/24* (2006.01)
*B01J 19/00* (2006.01)
*C07C 51/64* (2006.01)
*C07C 55/14* (2006.01)

(52) U.S. Cl.
CPC ................. *C07C 51/27* (2013.01); *B01J 8/24* (2013.01); *B01J 19/0013* (2013.01); *C07C 51/64* (2013.01); *B01J 2208/00371* (2013.01); *C07C 55/14* (2013.01)

(58) Field of Classification Search
CPC ......... C07C 51/27; C07C 51/64; C07C 55/14; B01J 8/24; B01J 19/0013; B01J 2208/00371
USPC ........................................................ 562/531
See application file for complete search history.

(56) References Cited

U.S. PATENT DOCUMENTS

| 6,822,117 B1 | 11/2004 | Felix et al. | |
| 2005/0070737 A1* | 3/2005 | Sutradhar | ............... C07C 51/42 562/590 |

OTHER PUBLICATIONS

International Search Report dated Feb. 27, 2019 in PCT/EP2018/084764 filed on Dec. 13, 2018.

* cited by examiner

*Primary Examiner* — Deborah D Carr
(74) *Attorney, Agent, or Firm* — Faegre Drinker Biddle & Reath LLP

(57) ABSTRACT

The present invention relates to a method of removing nitrate compounds from solid adipic acid.

19 Claims, No Drawings

METHOD OF REMOVING NITRATE COMPOUNDS FROM ADIPIC ACID

TECHNICAL FIELD OF THE INVENTION

The present invention relates to a method of removing nitrate compounds from solid adipic acid.

BACKGROUND

Commercially, adipic acid is produced from a mixture of cyclohexanol and cyclohexanone called "KA oil" (ketone-alcohol oil). The KA oil is oxidized with nitric acid to give adipic acid, via a multistep pathway. Side products of the method include glutaric acid and succinic acid.

Adipic acid is a major chemical intermediate used in particular as monomer in the manufacture of polymers, such as polyamides. The impurities obtained in the synthesis of adipic acid, such as glutaric acid and succinic acid, can degrade the quality of the polymers obtained. Therefore, impurities are usually removed before using the adipic acid in any polymerization process.

Initial product recovery and purification are accomplished through a crystallization of the reaction mixture followed by solid-liquid separation. Additional purification of adipic acid is accomplished through one or more steps of aqueous recrystallization followed by solid-liquid separation. The solid cake from the solid-liquid separation unit after the final recrystallization step typically contains about 3 to 14 wt. % of water.

The present inventors now found that the adipic acid obtained after purification by crystallization and solid-liquid separation still contains nitrate compounds in an amount which can affect the quality of polymers obtained from the adipic acid. It is therefore desirable to also remove at least part of these nitrate compounds from the solid adipic acid in order to further improve the quality of the polymers, such as polyamides, produced from the adipic acid.

SUMMARY OF THE INVENTION

The present inventors found that the above problem of removing at least part of nitrate compounds from solid adipic acid can be solved by contacting the adipic acid with a gas at an elevated temperature. In one embodiment, the present invention therefore relates to a method of removing at least part of nitrate compounds from solid adipic acid, said method comprising a first step of contacting the adipic acid comprising at least one nitrate compound with a gas and wherein the contacting takes place at a temperature in the range of above 80° C. to 95° C., and wherein
  a) the first step is not followed by any further step of contacting the adipic acid with a gas wherein the contacting takes place at a temperature higher than the temperature in the first step, or
  b) the first step is followed by a second step of contacting the adipic acid with a gas and wherein the contacting takes place at a temperature which is above the temperature in the first step but below 100° C.

In a further embodiment, the present invention relates to the use of a method which comprises contacting of adipic acid which comprises at least one nitrate compound with a hot gas for removing at least part of the at least one nitrate compound from the adipic acid.

In a further embodiment, the invention relates to the above use, wherein the method is the above method.

DETAILED DESCRIPTION

The invention relates to a method of removing at least part of nitrate compounds from solid adipic acid. The solid adipic acid can, for example, be obtained by oxidation of KA oil with nitric acid, crystallization of the thus obtained crude adipic acid from an aqueous solution followed by solid-liquid separation and optionally one or two recrystallization (s) followed by solid-liquid separation.

The adipic acid used in the method of the invention comprises at least one nitrate compound, such as inorganic or organic nitrate compounds, in particular nitrate salts. The concentration of nitrates in the adipic acid can be measured by UV-HPLC. A usual adipic acid which can be purified by the method of the invention can contain at least 2.0 ppm of nitrates, such as 2.5 to 10.0 ppm of nitrates, preferably 3.0 to 5.0 ppm of nitrates.

These and the following amounts of nitrates refer to the weight of $NO_3^-$ based on the total weight of the adipic acid including the nitrate compounds and optionally further impurities.

By using the method of the present invention, the amount of nitrate in the adipic acid can be reduced to less than 2.0 ppm, preferably less than 1.8 ppm, more preferably less than 1.6 ppm, such as for example 0.1 to less than 1.8 ppm, preferably 0.5 to less than 1.5 ppm.

The adipic acid comprising at least one nitrate compound used in the method of the invention may comprise further impurities, such as glutaric acid and succinic acid.

In the method of the invention, the adipic acid comprising at least one nitrate compound is contacted with a gas and contacting takes place at a temperature in the range of above 80° C. to 95° C. In a preferred embodiment the contacting takes place at a temperature in the range of 85° C. to 95° C., more preferably of 87° C. to 93° C., even more preferably of 88° C. to 92° C., and most preferably of 89° C. to 91° C.

The contacting can be conducted, for example, in a first compartment, chamber or vessel of a suitable apparatus for contacting a solid powder with a gas. Such apparatus can, for example, be a rotary drum or a fluidized bed. A fluidized bed being preferred.

The adipic acid comprising at least one nitrate compound can be fed into the compartment at any suitable temperature. For example, the adipic acid charged into the compartment can have ambient temperature of, for example, about 25° C.

In the compartment, the contacting of the adipic acid comprising at least one nitrate compound with a gas takes place at a temperature in the range of above 80° C. to 95° C. The temperature in the compartment can for example be adjusted by one or more heat exchangers. Additionally, it was found advantageous if the gas fed into the compartment has a temperature above the temperature at which contacting takes place. For example, the gas fed into the compartment can have a temperature in the range of above 110° C. to 150° C., preferably of 120° C. to 140° C., more preferably of 125° C. to 135° C.

Furthermore, the temperature in the compartment can be adjusted by using one or more, preferably one or two, heat exchangers in the compartment.

The temperature in the compartment and, thus, during the first step of the method of the invention is measured, for example, at the center of the compartment. Alternatively, the temperature can be measured at the outlet of the compartment where the adipic acid leaves the compartment and, thus, the first step of the method of the invention.

It was surprisingly found that the simple contacting of the adipic acid comprising at last one nitrate compound with a gas at a temperature in the range of above 80° C. to 95° C. is sufficient to remove at least part of the nitrate compounds from the solid adipic acid. The time of contacting the adipic acid comprising at least one nitrate compound with the gas required for removing at least part of the nitrate compounds is not particularly limited and can be selected by a person skilled in the art, for example, according to the desired amount of nitrates in the purified adipic acid.

Since the single step of contacting the adipic acid comprising at least one nitrate compound with a gas at a temperature in the range of above 80° C. to 95° C. is sufficient to remove at least part of the nitrate compounds, it is not necessary to further heat the adipic acid obtained from the first step. In one embodiment, the method of the invention therefore does not comprise any further step of contacting the adipic acid with a gas, wherein the contacting takes place at a temperature higher than the temperature of the first step.

It is, however, also possible and in some cases desirable that the first step is followed by a second step of contacting the adipic acid with a gas, wherein the contacting takes place at a temperature which is above the temperature in the first step but below 100° C., such as in the range of above 95° C. to less than 100° C., preferably in the range of above 95° C. to less than 99° C. This second step can, for example, be advantageous if the amount of nitrates in the adipic acid after the first step is still above the desired limit. With the second step, the amount of nitrates can then be further reduced.

Like the first step, also the second step of the method of the invention can be conducted in a compartment, chamber or vessel, such as a rotary drum or a fluidized bed. To further heat the adipic acid obtained from the first step to the contacting temperature of the second step, one or more heat exchangers may be used. Additionally, it was found advantageous if the gas fed into the compartment has a temperature above the temperature at which contacting takes place. For example, the gas fed into the compartment can have a temperature in the range of above 110° C. to 150° C., preferably of 120° C. to 140° C., more preferable of 125° C. to 135° C.

The temperature of the gas fed to the first step and to the second step can be the same or different, preferably the gas fed to the first step and to the second step has the same temperature.

The time of contacting the adipic acid with the gas in the second step is not particularly limited and can be selected by a person skilled in the art such that the adipic acid obtained from the second step has the desired low content of nitrates. For example, the overall contacting time in the first and, if present, second step can be in the range of from 15 to 100 minutes.

The temperature in the second step can be measured like the temperature in the first step.

Both, the first step and the second step, may each comprise only one step which each is conducted in a single compartment, such as the above described rotary drum or fluidized bed. Alternatively, each of the first step and the second step may comprise two or more consecutive steps of contacting the adipic acid with the gas. In the first step, in each of the consecutive steps the contacting takes place at a temperature in the range of above 80° C. to 95° C. In the second step, in each of the consecutive steps the contacting takes place at a temperature which is above the temperature in the first step but below 100° C.

Each of the compartments in which the steps of the method according to the invention and, in particular, according to the above embodiments are conducted, may contain one or more, preferably one or two heat exchangers for adjusting the temperature at which the adipic acid is contacted with the gas.

Preferably, the gas used in the method of the invention does not react with adipic acid at the temperature at which it is contacted with the adipic acid. For example, the gas can be selected from the group consisting of air, oxygen depleted air, nitrogen, superheated steam and mixtures of two or three thereof. The preferred gas is oxygen depleted air, which more preferably has a maximum oxygen content of 5 wt. % based on the total weight of the gas.

In the first step and the second step, different gases or the same gas may be used. Preferably, in both steps the same gas, in particular oxygen depleted air, is used. If the first step and/or the second step comprises two or more consecutive steps, the gas used in each of these steps may be the same of different, preferably in all steps the same gas, in particular oxygen depleted air, is used.

In one embodiment, the method of the invention further comprises the step of cooling the hot adipic acid from which at least part of the nitrate compounds have been removed to a temperature of below 50° C., preferably below 40° C., such as about 37° C. The cooling can be conducted, for example, by using a gas, such as air or nitrogen or oxygen depleted air, preferably oxygen depleted air, having a temperature of below 30° C., preferably below 20° C., such as about 15° C. The cooling is conducted by contacting the hot adipic acid with the cooling gas. Such contacting can take place in a compartment, chamber or vessel, such as a rotary drum or fluidized bed. A fluidized bed being preferred.

Also in the cooling step, one or more, preferably one or two heat exchangers may be employed for adjusting the temperature.

The cooling step may comprise one step or two or more consecutive steps in which the adipic acid is contacted with the cooling gas.

The time of contacting the adipic acid with the gas in the cooling step is not particularly limited and can be selected by a person skilled in the art such that the adipic acid obtained from the cooling step has the desired temperature. For example, the overall contacting time in the cooling step can be in the range of from 15 to 60 minutes.

In one embodiment, all steps of the method of the invention are conducted in fluidized beds.

Where the gas is fed to fluidized bed(s), the gas flow can be set to, for example, 0.1 m/s to 1.0 m/s, preferably 0.2 m/s to 0.8 m/s, more preferably to 0.3 m/s to 0.5 m/s.

The second step can directly follow to the first step or the method of the invention can comprise one or more further step(s) between the first step and the second step.

Also the cooling step can directly follow to the first step or the second step. Alternatively, there can be one or more further step(s) between the first step and the cooling step or the second step and the cooling step.

The adipic acid comprising at least one nitrate compound used in the method of the present invention can be dry or moist. Advantageously, the adipic acid comprising at least one nitrate compound being fed to the first step of the method of the invention is moist because usually the adipic acid obtained from crystallization and solid-liquid separation is moist. For example, the water content of the adipic acid comprising at least one nitrate compound is at least 3 wt. % of its total weight, preferably the water content is in the range of 3 wt. % to 14 wt. %, more preferably in the range of 9 wt. % to 14 wt. %, each of the total weight of the adipic acid comprising at least one nitrate compound.

The method of the present invention can be conducted batchwise or continuously. The method can also be conducted partly batchwise and partly continuously, for example, by conducting the first step in one batch and then conducting the second step and the cooling step continuously. Other combinations are possible as well. Conducting the method of the invention continuously is preferred.

In a further embodiment, the present invention relates to the use of a method which comprises contacting of adipic acid which comprises at least one nitrate compound with a hot gas for removing at least part of the at least one nitrate compound from the adipic acid. The gas as well as its temperature can be selected as described above. In a preferred embodiment of this use, the method is as described above including its preferred embodiments.

The following example is given by way of non-limiting illustration of the present invention, and variations thereof that are readily accessible to a person skilled in the art.

Example

Moist adipic acid containing 12.9 wt. % of water and 3 to 5 ppm of nitrates and having ambient temperature was fed to a fluidized bed dryer having two main compartments, a hot compartment and a cold compartment. The hot compartment was separated in two compartments, which were both fed with nitrogen gas having a temperature in the range of 130° C. to 135° C. The adipic acid was continuously fed into the first compartment and continuously moved from the first hot compartment to the second hot compartment. By using heat exchangers the temperature in the first hot compartment was adjusted to about 89° C. while the temperature in the second hot compartment was adjusted to about 98° C. From the second hot compartment the adipic acid was transferred to a cold compartment comprising heat exchangers. The cold compartment was fed with cold nitrogen gas. By using the heat exchangers and the cold gas, the temperature of the adipic acid at the outlet of the dryer was about 37° C.

The fluidized bed dryer was run for a total of six days using the above parameters and settings. The adipic acid obtained had a content of nitrates in the range of 1 to 1.5 ppm.

The invention claimed is:

1. A method of removing a nitrate compound from solid adipic acid, said method comprising:
   i) contacting solid adipic acid comprising a nitrate compound with a gas, wherein the contacting takes place at a temperature in a range of above 85° C. to 95° C., wherein i) is either:
   a) not followed by any further contacting of the solid adipic acid with a gas wherein the further contacting takes place at a temperature higher than the temperature of i), or
   b) followed by further contacting the solid adipic acid with a gas wherein the further contacting takes place at a temperature that is above the temperature of i) above 95° C., but below 100° C.

2. The method of claim 1, wherein i) comprises one step or two or more consecutive steps of contacting the solid adipic acid with the gas and wherein in each of the two or more consecutive steps the contacting takes place at a temperature in the range of above 80° C. to 95° C.

3. The method of claim 1, wherein the further contacting of b) comprises one step or two or more consecutive steps of further contacting the solid adipic acid with the gas and wherein in each of the two or more consecutive steps the further contacting takes place at a temperature which is above the temperature of i) but below 100° C.

4. The method of claim 1, wherein, in i), the contacting takes place at a temperature in a range of 85° C. to 95° C.

5. The method of claim 1, wherein a gas fed to i) and/or the further contacting of b) has a temperature in a range of above 110° C. to 150° C.

6. The method of claim 1, wherein a gas fed to i) and a gas fed to the further contacting of b) have the same temperature.

7. The method of claim 1, wherein the gas does not react with adipic acid at the temperature at which it is contacted with the adipic acid.

8. The method of claim 1, further comprising:
   ii) cooling hot adipic acid from which the nitrate compound has been removed to a temperature of below 50° C.

9. The method of claim 8, wherein the cooling is conducted using a gas.

10. The method of claim 1, wherein, in each of i) and the further contacting of b), one or more heat exchangers are employed for adjusting the temperature.

11. The method of claim 1, herein the contacting of the solid adipic acid with the gas is conducted in one or more fluidized beds.

12. The method of claim 11, wherein the gas is fed to the one or more fluidized beds at a gas flow of 0.1 m/s to 1.0 m/s.

13. The method of claim 1, wherein solid adipic acid comprising the nitrate compound fed to i) is moist.

14. The method of claim 1, wherein the solid adipic acid comprising the nitrate compound is obtained by:
   oxidizing a mixture comprising cyclohexanol and cyclohexanone with nitric acid, to obtain crude adipic acid,
   crystallizing the crude adipic acid from an aqueous solution followed by solid-liquid separation, to obtain adipic acid, and
   recrystallizing one or two time(s) the adipic acid from an aqueous solution followed by solid-liquid separation.

15. The method of claim 1, wherein the i) contacting takes place at a temperature in a range of 89° C. to 95° C., and is followed by further contacting the solid adipic acid with the gas at a temperature of 98° C. to below 100° C.

16. The method of claim 15, wherein, after contacting the solid adipic acid with the gas at a temperature of 98° C. to below 100° C., the amount of the nitrate compound present in the solid adipic acid is from 20% to 50% of the amount of the nitrate compound present in the solid adipic acid before the i) contacting.

17. The method of claim 1, wherein after (a) or (b) the amount of the nitrate compound present in the solid adipic acid is from 20% to 50% of the amount of the nitrate compound present in the solid adipic acid before the i) contacting.

18. The method of claim 15, wherein a time for the i) contacting and a time for the further contacting are the same.

19. The method of claim 1, wherein the i) contacting takes place at a temperature in a range of 85° C. to 89° C., and is followed by further contacting the solid adipic acid with the gas at a temperature of 95 to 98° C.

* * * * *